(12) United States Patent
Pahuja et al.

(10) Patent No.: US 7,935,366 B2
(45) Date of Patent: May 3, 2011

(54) CALCIUM POTASSIUM FERROCYANIDE, A PROPHYLACTIC MIXTURE COMPRISING THIS COMPOUND AND THE USE THEREOF FOR DECORPORATION OF RADIOCESIUM IN SUBJECTS AFFECTED BY NUCLEAR RADIATION

(75) Inventors: Dharampal Nandiram Pahuja, Parel (IN); Vikram Sarjerao Jagtap, Parel (IN); Vinay Ramkrishna Sonawane, Parel (IN)

(73) Assignee: Secretary, Department of Atomic Energy, Mumbai (IN)

( * ) Notice: Subject to any disclaimer, the term of this patent is extended or adjusted under 35 U.S.C. 154(b) by 758 days.

(21) Appl. No.: 11/794,781

(22) PCT Filed: Jan. 10, 2006

(86) PCT No.: PCT/IN2005/000012
§ 371 (c)(1),
(2), (4) Date: Feb. 5, 2008

(87) PCT Pub. No.: WO2006/072962
PCT Pub. Date: Jul. 13, 2006

(65) Prior Publication Data
US 2008/0145448 A1    Jun. 19, 2008

(51) Int. Cl.
| | |
|---|---|
| A61K 9/20 | (2006.01) |
| A61K 33/00 | (2006.01) |
| A61K 33/26 | (2006.01) |
| A61K 33/10 | (2006.01) |
| A01N 59/24 | (2006.01) |
| A01N 59/16 | (2006.01) |
| A01N 59/22 | (2006.01) |
| A01N 59/06 | (2006.01) |

(52) U.S. Cl. ........ 424/687; 424/464; 424/610; 424/648; 424/667; 424/668

(58) Field of Classification Search ........................ None
See application file for complete search history.

(56) References Cited

U.S. PATENT DOCUMENTS

| | | |
|---|---|---|
| 2,780,238 A | 2/1957 | Davies et al. |
| 5,288,718 A | 2/1994 | Varga et al. |
| 5,403,862 A | 4/1995 | Miller et al. |
| 5,494,935 A | 2/1996 | Miller et al. |

FOREIGN PATENT DOCUMENTS

| | | |
|---|---|---|
| DE | 3735204 | 4/1989 |
| GB | 287482 | 9/1928 |
| WO | WO 97/32816 | 9/1997 |
| WO | WO 99/10278 | 3/1999 |
| WO | WO 00/50046 | 8/2000 |

OTHER PUBLICATIONS

Thompson et al. (Abstract of Pharmacotherapy 2001, 21(11), 1364-7).*
Jagtop et al. (Abstract of J Radiol Prot 2003, 23(3), 317-26).*
Shenolikar et al. (Journal of Nuclear Medicine 1973, 14(1), pp. 2-4).*
Kirichenko, I. Ya. et al., "Preparation of Potassium Ferrocyanide," Extrait de Brevet Russe (Derwent), 1964, p. 1-3.
Grutzner A., "Gmelins Handbuch der Anorganischen Chemie," Verlag Chemie, Weinheim, System nr 59, Teil B, 1932, p. 1-5.
Grutzner A., "Gmelins Handbuch der Anorganischen Chemie," Verlag Chemie, Weinheim, System nr 59, Teil B, 1932, p. 1-5 (English Translation).
International Search Report for PCT/IN2005/000012, Jan. 10, 2008.

* cited by examiner

*Primary Examiner* — Ernst V Arnold
(74) *Attorney, Agent, or Firm* — Merchant & Gould P.C.

(57) ABSTRACT

A new prophylactic mixture is prepared for the effective decorporation of *Cs, *Sr, *I from affected subjects in the event of an accidental release of the radioisotopes in the environment due to any nuclear accident. The prophylactic mixture comprising: 1) Calcium Potassium Ferrocyanide [$CaK_2Fe(CN)_6$] 2) Calcium Iodate, and 3) Calcium Carbonate, can be formulated in the form of a single tablet, capsule or suspension for easy administration to the radiation affected subjects in cases of emergency or nuclear fallout. Also claimed are the compound calcium potassium ferrocyanide ($CaK_2Fe(CN)_6$) and the use thereof for decorporation of *Cs in subjects affected by nuclear radiation.

15 Claims, 4 Drawing Sheets

CALCIUM POTASSIUM FERROCYANIDE, A PROPHYLACTIC MIXTURE COMPRISING THIS COMPOUND AND THE USE THEREOF FOR DECORPORATION OF RADIOCESIUM IN SUBJECTS AFFECTED BY NUCLEAR RADIATION

FIELD OF INVENTION

The invention relates to a prophylactic mixture for the simultaneous decorporation of Radiocesium (*Cs), Radiostrontium (*Sr) and Radioiodine (*I) from in vivo milieu of subjects affected by the exposure to nuclear radiation.

BACKGROUND AND PRIOR ART

Nuclear fission in the experimental, isotope-producing, or energy-supplying nuclear reactors and in nuclear weapon tests is accompanied by the formation of a considerable amount of radioactive by-products. Majorities of these hot materials involve fission products and activated elements, including extremely hazardous radioactive isotopes such as iodine-131, strontium-89-90, cesium-134 and -137, cerium-141 and -144. Emitted into the environment, they may result in a radioactive pollution.

There are three ways these isotopes can enter the human body: the respiratory tract (breathing with air), the digestive tract (ingesting with foods and drinks), the epidermal layer of the skin (contacting with harmed or unharmed skin).

A good deal of methods are already known for reducing or even preventing injuries of health due to such radiation exposure. Some isotopes, essentially Radiostrontium, however, can only be protected against by hindering/preventing its gastrointestinal absorption with per oral administration of suitable adsorbents (blockers/congeners, which will block absorption of *Sr or compete with *Sr and hence, hinder its absorption). If the medical aid begins as late as several hours after the contamination, no efficient methods are available at the present state of the medical art for blocking the absorbed proportion of the radioisotopes, which could get transported by the blood-stream and the lymph-flow to influence their deposition in bones, to prevent their histic binding and to promote their decorporation.

Many of such radiological impacts in the event of any nuclear accident are ascribed to the exposure to the other volatile radionuclides, mainly Radiocesium (*Cs) and Radioiodine (*I), which could be effectively transported through the atmosphere to the "far-field", besides causing the immediate radiation hazard to the inhabitants in the "near-field" region. *Cs, with its wide distribution, its 30 year half-life and, its beta/gamma dose potential and its ubiquitous distribution throughout all tissues (because of being a Potassium congener) besides getting recycled through plant-animal-human food chain, poses the dominant radio-biological threat.

Radiostrontium (*Sr) is another radionuclide, which also needs to be attended to because of its long half-life of 28.5 years ($^{90}$Sr) besides its specific localization in bone, where it can damage the affected subjects' bone-marrow, once it enters in our in vivo milieu. Apart from $^{239}$Pu, which is basically fixed to the soil and has shown no significant transfer to man after the Chernobyl nuclear accident, only $^{137}$Cs and $^{90}$Sr have deposited on the ground and entered the biological cycle, besides Radioiodine induced damage to the thyroid gland in the early stages after a nuclear accident.

Of the various radioisotopes of Cesium (Cs), $^{137}$Cs is the most important and a common fission by-product material, besides being a frequent active component of sealed sources used for industrial/medical application. It is an important radionuclide, particularly in radiation oncology, found in hospitals performing either gynecological brachytherapy or intestinal therapy for solid tumors. All this has resulted in a steady increase in the use of *Cs for various experimental, diagnostic and therapeutic purposes. The presence of a large number of nuclear reactors world wide has further increased the chances of its accidental release, posing a greater radiation hazard, not only to workers at the reactor site and the people around but also to the population at a distance, if they are exposed to the air-borne *Cs or contaminated food/water. These risks have been clearly exemplified by the Chernobyl nuclear reactor and Goinnia radiological accidents.

Radio-cesium (*Cs), particularly $^{137}$Cs, has a high impact on human health for the following reasons:

1. It is easily absorbed by the body through different routes (ingestion, inhalation and/or skin penetration).
2. It has a relatively long biological half-life in humans of about 100-110 days.
3. Its physical half-life is 30 years.
4. It emits beta and penetrating gamma radiation of high energy.
5. It is distributed uniformly more or less throughout the body due to its proximity to elements Potassium and Sodium.

The most common treatment for metal poisoning is "chelation therapy." Conventional chelation therapy involves intravenous injection of a chelating agent into the patient. Widely known and conventional chelating agents such as EDTA (ethylenediaminetetraacetic acid) and DTPA (diethylenetriamine pentaacetic acid) are often employed. Conventional chelation therapy is very painful to the patient and has only limited effectiveness.

Moreover most of the chelating agents used in this type of therapy are generally hydrophilic, rapidly excreted, and have only limited ability to penetrate cells in order to remove the subject metals. Thus, the use of EDTA in the treatment of lead poisoning, for example, is effective in removing lead in the blood, but is not effective in removing lead that has penetrated (deposited in) the cells (vital tissue/organ).

Furthermore, it is not possible to target specific organs with conventional chelation therapy. Certain metals are more significantly deposited in certain organs than in other organs. Some metals, for example, are significantly deposited in the bone. Thus, in order to provide an effective treatment it is necessary to have a substance that can penetrate the cellular barrier lining the bone surface. This capability is not readily available with conventional chelating agents.

It is also of importance that the compositions promote decorporation of the metal, not redistribution of the metal. In some studies with known chelating agents it has been suggested that the metal is simply dislodged from one tissue and redeposited in another tissue. The compositions of the present invention, conversely, result in actual removal of the metal from the body of the mammal.

U.S. Pat. Nos. 5,494,935 and 5,403,862 teach several new chelating agents like partially lipophilic polyaminocaboxylic acids (PACA) for decorporation of heavy metal ions from the in vivo system of affected subjects. In contrast to their non-lipophilic counterparts EDTA and DTPA, these chelating agents exhibit appreciable absorption from the intestine and therefore, can be administered orally. But, the deficiency associated with such chelating agents is that they can be directed primarily to certain specific organs only. Moreover, these chelating agents target only some particular adsorbed metals, and not specifically their radioactive counterparts.

U.S. Pat. No. 5,288,718 discloses monocyclic cryptate ligands and their derivatives that are suitable for the removal of Radiostrontium, occasionally other radioactive metal isotopes, from the living organisms. An active agent based on 1,4,10,13-tetraoxa-7, 16diazacyclooctadecane-N, N'-dimalonic acid tetrasodium salt was shown to be capable of promoting the excretion of Radiostrontium and Radiocesium which had been administered into various sites (peritoneal cavity, subcutaneous interstitial tissue, lung) of the animal body.

U.S. Pat. No. 4,780,238 relates to the preparation of new, naturally produced chelating agents as well as to the method and resulting chelates of desorbing cultures in a bioavailable form involving Pseudomonas species or other microorganisms. A preferred microorganism is Pseudomonas aeruginosa which forms multiple chelates with thorium in the range of molecular weight 100-1,000 and also forms chelates with uranium of molecular weight in the area of 100-1,000 and 1,000-2,000.

Hitherto, Prussian blue (as Radiogardase-Cs, marketed by Heyl, Chem. -Pham, Fabrik, Berlin) has been in use for the clearance of *Cs from in vivo milieu. Chemically, it is insoluble ferric hexa-cyanoferrate (II) with an empirical formula of $Fe_4[Fe(CN)_6]_3$ and a molecular weight of 859.3 Dalton. It is provided as blue powder in 0.5 g gelatin capsules.

Hitherto reported mixture of three compounds: Prussian blue, Calcium Alginate (CaA) and Potassium Iodide (KI), is suggested to be mixed in the diet and fed for three days earlier to the animals before their exposure to the radionuclides, for their clearance from the in vivo milieu.

There are several drawbacks associated to the hitherto known processes, which the present invention seeks to remove, namely:

1) Prussian blue, Calcium alginate and KI need to be mixed with the diet and fed prior to the exposure to the radionuclides, which is not always feasible.
2) Prussian blue is slow in removing *Cs from in vivo system of the experimental animals. One of the constituents—Calcium Potassium Ferrocyanide [$CaK_2Fe(CN)_6$], of the present mixture is considerably faster than Prussian blue in decorporating *Cs from the in vivo system of the experimental animals.
3) Prussian blue induces gastro-intestinal and cardio-toxicity in the experimental animals. The present mixture does not produce any such histo-pathologic changes in these organs. Prussian Blue also produces significantly more liver and kidney damage compared to Calcium Potassium Ferrocyanide, when fed in the diet or administered orally at the same dose level as Prussian Blue, for approximately six months.
4) Prussian Blue has been observed to induce constipation in some subjects probably because of gastro-intestinal toxicity.
5) Mild reduction in hemoglobin levels has been noted in the animals after treating with the hitherto reported mixture of antidotes.
6) Prussian blue, at the same dose level, is only 25-50% as effective as Calcium Potassium Ferrocyanide [$CaK_2Fe(CN)_6$], a constituent of the present mixture, in complexing/extraction of stable/radio Cesium, in acidic medium (pH 2-3) normally present in the gastric region.
7) Calcium alginate, an ingredient of the hitherto known mixture, is quite viscous and unpalatable compound compared to one of the common calcium salts used in the mixture. The calcium based salt used in the present mixture, is as potent as Calcium alginate in curtailing whole body retention of *Sr.
8) KI, used in the hitherto known mixture, is known to be quite hygroscopic chemical and thus reduces the shelf life of the mixture. This poses storage problems.
9) Remedial measures are specific for a particular radionuclide and not others and in case individuals have been exposed to more than one radionuclide, they need to be treated for each radio-isotope separately.

Thus, there is a long felt need for a suitable radio decorporating agent, which could remove these drawbacks connected to the prior art. The following specific requirements are established to such a prophylactic agent:

(a) the complex formation must take place in the biological system even in the presence of concurrent ions (such as $Ca^{2+}$, $Na^+$, $K^+$, etc.) and ligands that are present in a great amount.

(b) it should have a pharmaceutically acceptable level of toxicity (wide-range efficiency);

(c) it must be easily administrable.

The inventors have found that the retention of three most important fission radionuclides: *Cs, *Sr and *I may be simultaneously curtailed and decorporated from subjects accidentally exposed to such radionuclides, by the oral administration of a mixture of:

(a) Calcium Potassium Ferrocyanide [$CaK_2Fe(CN)_6$]—a novel compound;

(b) Calcium Iodate, and (c) Calcium Carbonate.

The detailed formulation of such a mixture is provided in the following section.

OBJECTS OF THE INVENTION

It is an object of the invention to provide a prophylactic mixture which affects the efficient removal of all three radionuclides *Cs, *Sr and *I, simultaneously from the in vivo system of affected subjects, thus eliminating the need for them to be decorporated separately.

Another object of the invention is to provide for a more effective and convenient mixture than the hitherto reported mixture of Prussian blue, Calcium alginate and KI for the simultaneous decorporation of *Cs, *Sr and *I from the in vivo milieu of the affected humans and animals.

Another object of the Invention is to provide new and comparatively non-toxic, more stable and more palatable decorporators for the clearance of *Cs, *Sr and *I, as compared to the currently used Prussian Blue, Calcium Alginate and Potassium Iodide.

Another object of the invention is that the said prophylactic mixture can also be sweetened and prepared as a single chewable tablet which can be administered very easily to the affected population (humans and animals) in a disturbed scenario following an radiological or nuclear emergency.

SUMMARY OF THE INVENTION

Thus, the invention relates to a prophylactic mixture for efficient removal of fission radionuclides *Cs, *Sr and *I from subjects exposed to such dangerous radiation, said mixture comprising:
1) Calcium Potassium Ferrocyanide—[$CaK_2Fe(CN)_6$]
2) Calcium Iodate [$Ca(IO_3)_2$]
3) Calcium Carbonate ($CaCO_3$)

The formulation according to the invention is in the form of tablets, capsules, kit or suspension or the like. The constituents can be formulated in smaller doses of 50% of an adult dose to be suitable for children.

DETAILED DESCRIPTION OF THE INVENTION

Figure 1:
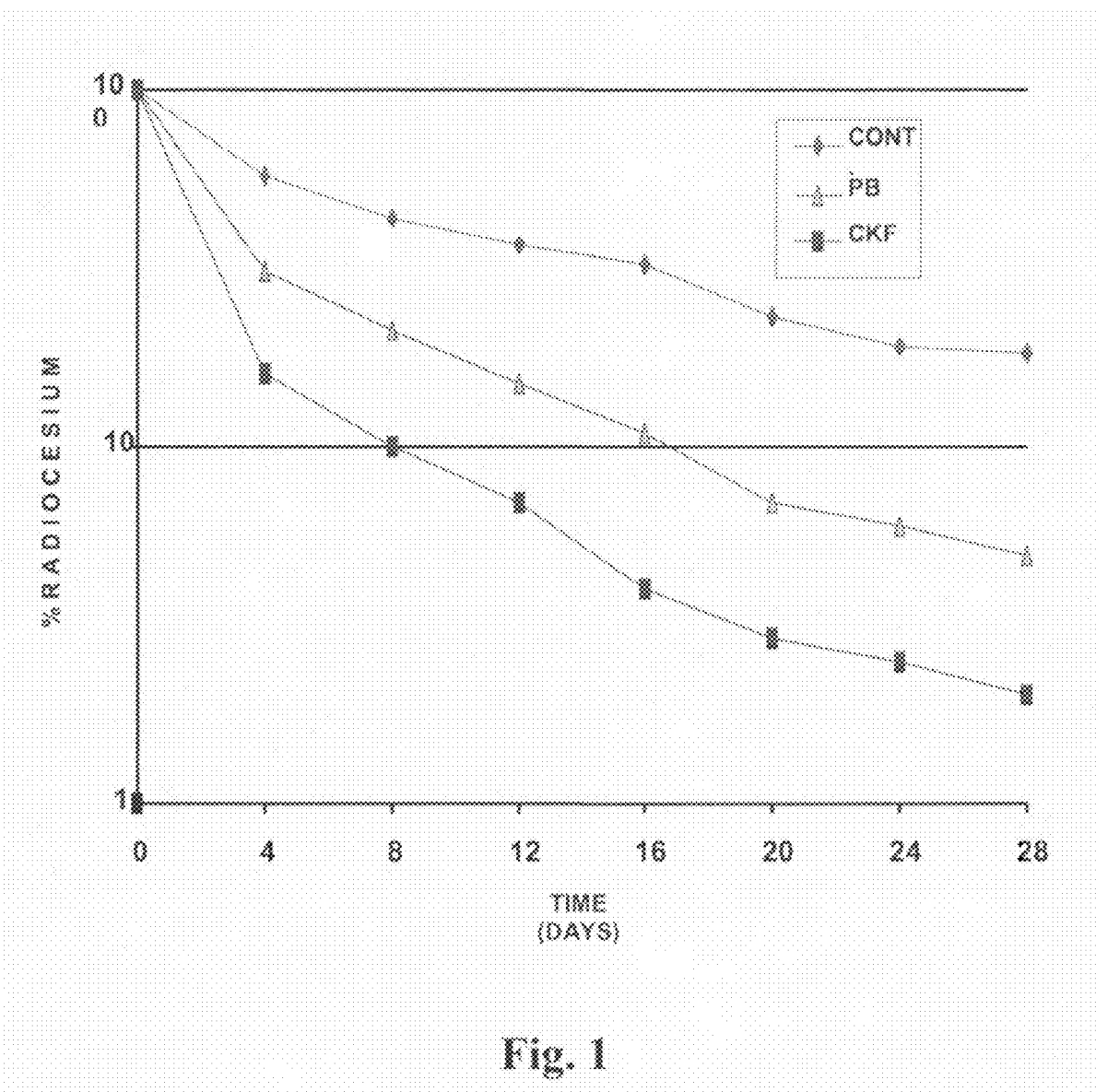
FIG. 1 shows graphically the whole body retention of *Cs using [$CaK_2Fe(CN)_6$] vs. Prussian Blue. The graph clearly shows that [$CaK_2Fe(CN)_6$], when used solely for *Cs decorporation is twice as effective as Prussian Blue.
Figure 2:
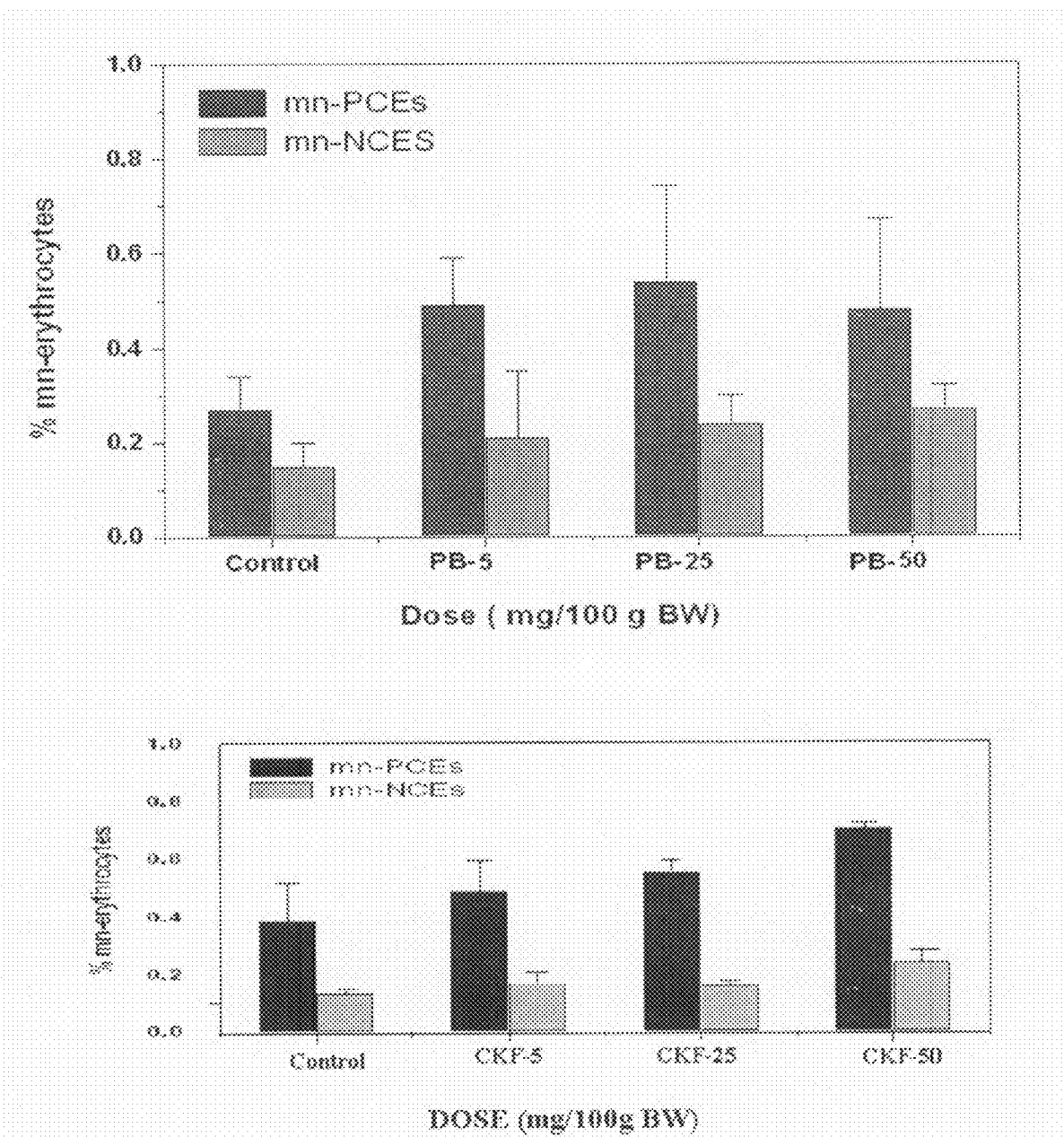
FIG. 2 shows the geno-toxicity data showing the effect of Prussian Blue and [$CaK_2Fe(CN)_6$] on micronuclei formation in rat bone marrow erythrocytes. The geno-toxicity assessment of [$CaK_2Fe(CN)_6$] and Prussian Blue for the formation of micronuclei (i.e. part of parent nucleus, which is left behind in the cytoplasm as a daughter nuclei, due to damage to chromosomes during cell division). These figures reveal that both [$CaK_2Fe(CN)_6$] and Prussian blue are quite non-toxic as they did not induce any toxicity at the dose of 5 mg/100 g BW (equivalent to 3.5 g/d/70 Kg adult) of test compounds. It has also been observed that five and ten times of this dose induces marginal increase in the formation of micronuclei. The means±SE are, however, not significantly different from control at all the tested doses.
Figure 3:
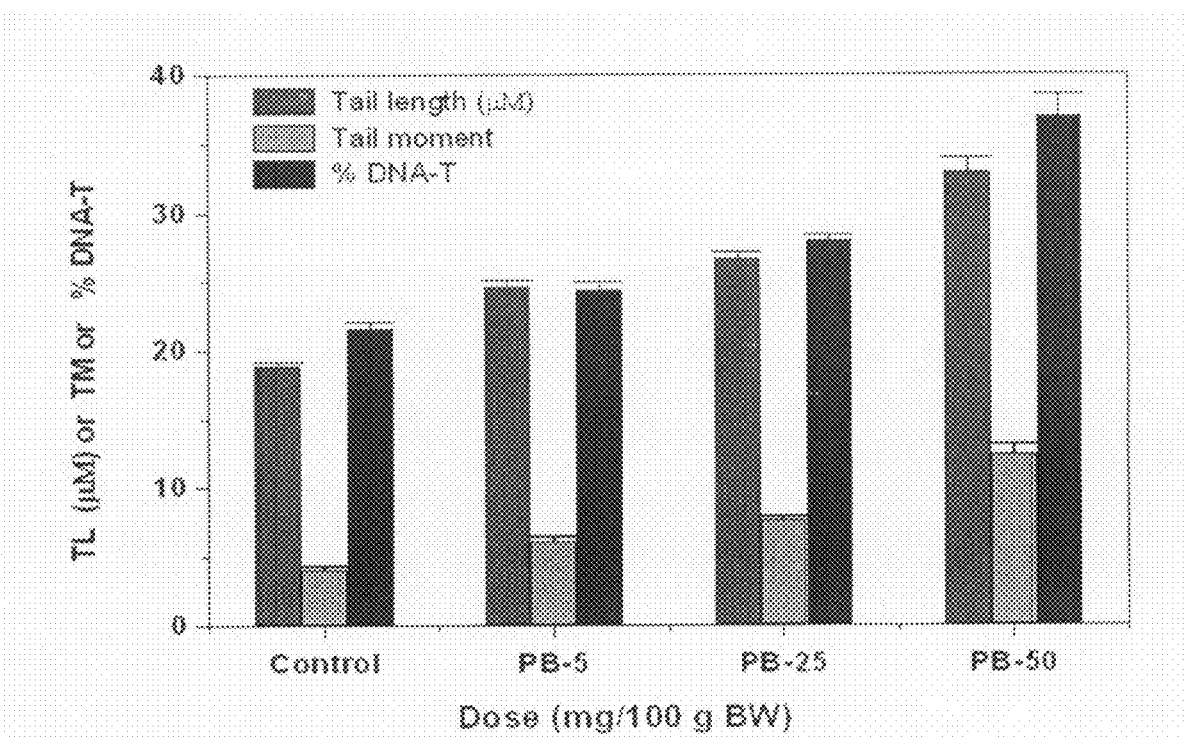
FIG. 3 showing the results of alkaline comet assay also demonstrates that both PB and CKF are not significantly different from control and do not induce any apparent DNA damage.
Figure 3:
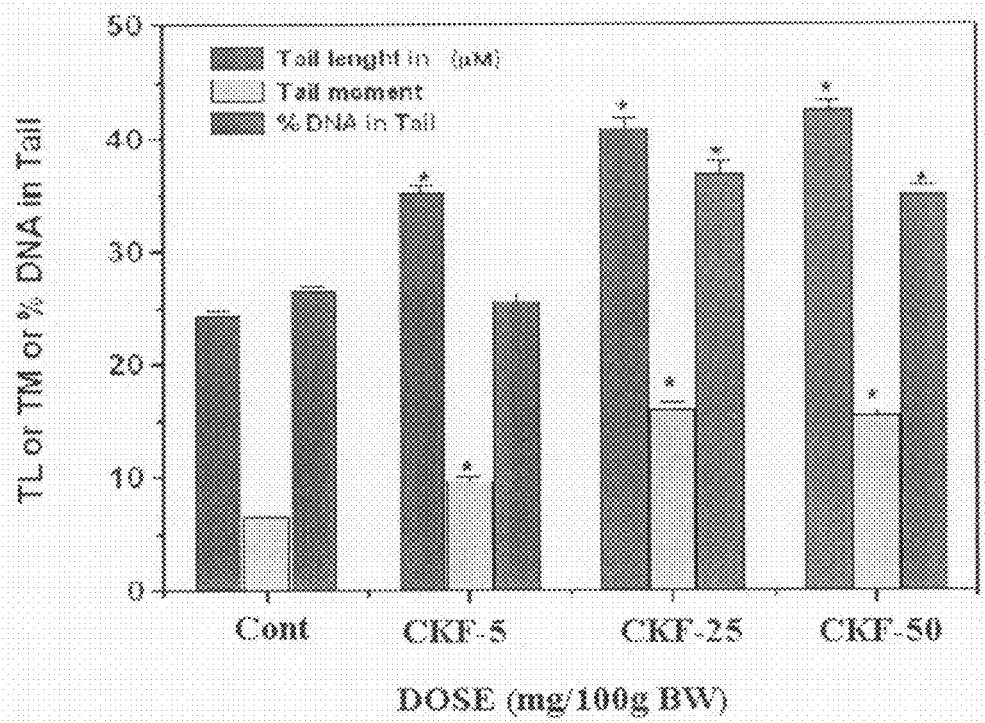
Figure 4:
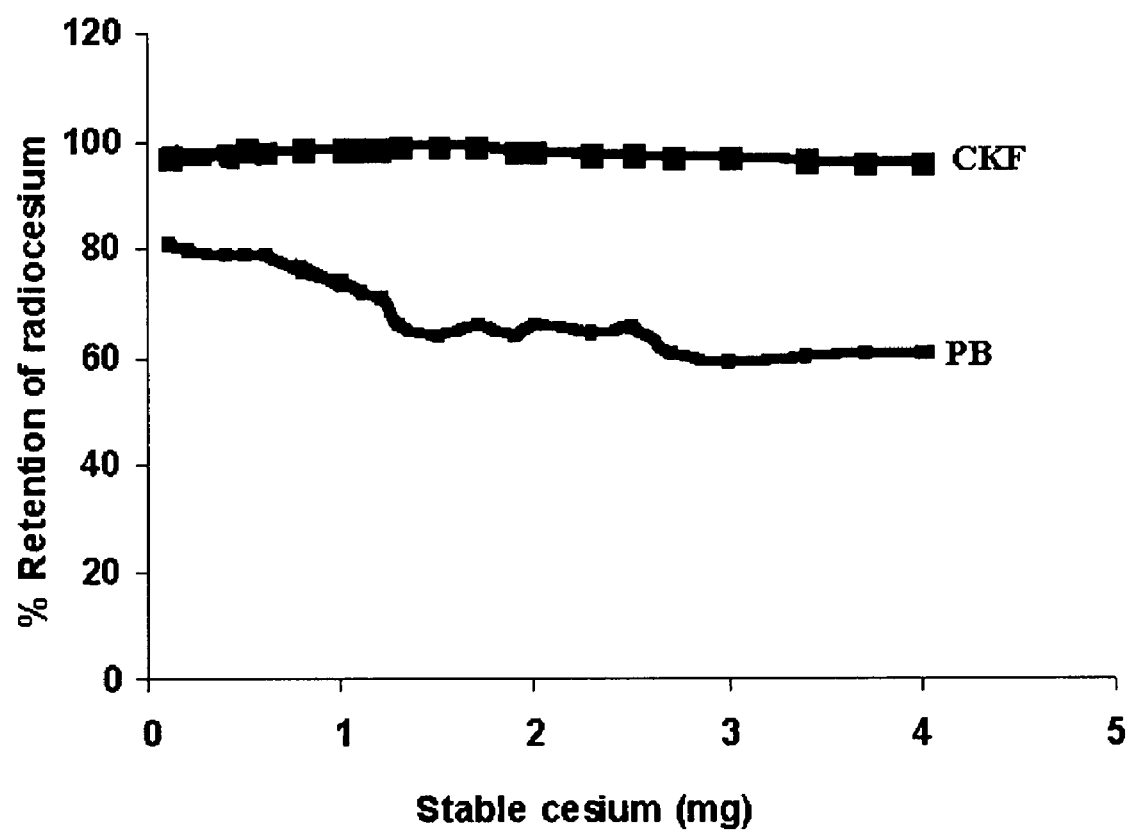
FIG. 4 further demonstrates the firm binding of CKF with *Cs even at neutral pH compared to PB, which shows weaker binding.

The invention encompasses the formulation of a prophylactic mixture used for the decorporation of the known radionuclides in the event of their release in the environment. The mixture is sparingly soluble and has a long shelf life and it is not affected even by the hot and humid climate of a tropical country like India. It can be stored as water suspension but preferably in tablet/capsular form. The mixture according to the invention comprises:
(a) Calcium Carbonate ($CaCO_3$): 1000-1500 mg, more preferably 1100-1400 mg, most preferably 1200-1300 mg being equivalent to 480-520 mg of elemental calcium.
(b) Calcium Iodate [$Ca(IO_3)_2$]: 45-65 mg, more preferably 50-60 mg, most preferably 52-56 mg being equivalent to ~33 mg of stable iodine.
(c) Calcium Potassium Ferrocynide [$CaK_2Fe(CN)_6$]: 900-1100 mg, more preferably 950-1050 mg, most preferably 980-1020 mg.

The above mixture (most preferably weighing 2.2-2.4 g) can be made as a suspension in 15 ml of drinking water, or soda or soft drink or fruit juice or sweetened as chewable tablet or formulated in tablets/capsules to be swallowed with water, and this dose needs to be ingested by an adult person two to three times a day (equivalent to a total of ~30-45 ml suspension or equivalent to 4-6 tablets/capsules of the prophylactic mixture) depending upon the severity of radiation contamination in the event of radiation emergency.

Calcium carbonate ($CaCO_3$) is used for the decorporation of Radiostrontium (*Sr). Calcium Iodate is as effective as $KI/KIO_3$ in blocking Radioiodine (*I) uptake by the thyroid gland. [$CaK_2Fe(CN)_6$] is used for the enhanced clearance of Radiocesium (*Cs) from in vivo system.

The analysis of [$CaK_2Fe(CN)_6$] suggests that it is an insoluble compound, hitherto not known for any of its use and effect as demonstrated in this invention. It can be synthesized from two commonly used compounds: Potassium Ferrocyanide [$K_4Fe(CN)_6$] and calcium chloride, $CaCl_2$. It is incorporated with two elements, Calcium and Potassium, which are not present in Prussian blue. These two extra elements (most particularly Calcium) in its nucleus make it more potent than Prussian blue in clearing *Cs from in vivo system. Its structure is shown by structural formula I as follows:

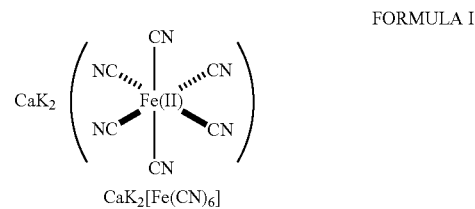

FORMULA I $CaK_2[Fe(CN)_6]$

The other two ingredients of the mixture, namely Calcium Carbonate and Calcium Iodate are commercially available.

The present invention further relates to an easy and efficient process for the preparation of Calcium Potassium Ferrocyanide, the said process comprising the steps of:
(a) taking 250 ml of aqueous 0.5 mole solution of Potassium Ferrocyanide —$K_4Fe(CN)_6$. $6H_2O$ in a 2 litre flask;
(b) Adding 250 ml of 1 mole solution of aqueous Calcium Chloride dihydrate $CaCl_2$.2 $H_2O$, drop wise with continuous vigorous stirring to the solution in (a);
(c) allowing the precipitate formed to settle overnight;
(d) separating the supernatant solution from the precipitate by decantation and by mild suction by the application of a mild vacuum;
(e) washing the precipitate with warm water to remove the traces of soluble impurities;
(f) subsequently washing with acetone to remove traces of water
(g) allowing the yellow precipitate obtained thus to dry for 8 hours at 90° C.;

The yield of the final compound obtained by this product is about 80%.

The aforesaid mixture can further be formulated in smaller doses (approximately 50% of the adult dose) for administration to the children as follows:
(a) Calcium carbonate ($CaCO_3$): 500-750 mg, more preferably 550-700 mg, most preferably 600-650 mg equivalent to 240-260 mg of elemental calcium.
(b) Calcium iodate [$Ca(IO_3)_2$]: 20-35 mg, more preferably 25-30 mg, most preferably 26-28 mg, equivalent to ~16 mg of stable iodine.
(c) Calcium Potassium Ferrocynide [$CaK_2Fe(CN)_6$]: 450-550 mg, more preferably 475-525 mg, most preferably 490-510 mg.

The above prophylactic mixture (most preferably weighing 1.1-1.2 g) can be made as a suspension in 7.5 ml of drinking water, or soda or soft drink or fruit juice or formulated as chewable tablet or formulated in two smaller tablets/capsules to be swallowed with water and this dose need to be ingested by a child two to three times a day (equivalent to a total of ~15-22.5 ml suspension or equivalent to 4-6 tablets/capsules of the prophylactic mixture) depending upon the severity of radiation contamination in the event of radiation emergency.

The said mixture can be formulated in a suspension form or preferably in the form of a tablet or a capsule. The said tablets or capsules can be easily dispensed to the affected people in the emergency situations at the nuclear reactor site. It can be conveniently dispensed/distributed to all of the affected people.

The appropriate dosing for the mixture would depend upon the age, weight etc. of the affected subject as well as the severity of contamination. The suspension, both in adult dosage form as well as the child dosage form, can also be administered by stomach-tube (gastric lavage) if the affected subject is not in a position to take it orally if such an emergency situation arises.

The prophylactic mixture releases free/extra calcium in the gastrointestinal system, which has been found to provide the following further advantages:
1. Calcium in the gastro-intestinal lumen is very useful for complexing and clearing from our in vivo milieu, quite a few undesirable/toxic substances.
2. Calcium also blocks the active transport mechanism in the intestine by slowing down/stopping the synthesis of (active) hormonal form of vitamin D, which stimulates rapid absorption of calcium and some other elements.
3. Calcium competes with the elements like strontium for their absorption by passive diffusion.
4. Calcium also helps to retard cell membrane damage.
5. Calcium also plays an important role in the modulation of anti-oxidant defense mechanism by stabilizing vitamin E, Glutathione and Protein-thiols, which are known to be the major players in scavenging the free radicals, normally known to be increased due to the impact of radiation.

It has also been noted that the Calcium salts used in the mixture also help in decorporating stable Cesium as well as Thallium and stable Strontium, which are quite toxic and are used in many industrial and biomedical applications.

The tablets and capsules can be prepared by any of the methods known to a person skilled in the art.

Reference is now drawn to Table 1 as hereunder which shows comparatively the effect of the present mixture vis-à-vis the mixture of Prussian Blue, $KIO_3$ and Calcium Alginate mixed in the diet and given orally after the administration of cocktail of *Cs+*Sr+*I. The experimental animals were given orally this new prophylactic mixture of decorporators, 2 hours after the oral administration of a cocktail of three radionuclides (*I, *Cs and *Sr), and the whole body retention of each radionuclide was measured after 24 hours to 14 days. This has been compared to the mixture of Prussian Blue (PB)+$KIO_3$+Calcium Alginate, which can only be fed in the diet.

TABLE 1

COMPARISON OF PRESENT MIXTURE [[$CaK_2Fe(CN)_6$], + $Ca(IO_3)_2$ + $CaCO_3$] WITH (PB + $KIO_3$ + Ca-Alginate) MIXTURE ON THE WHOLE BODY RETENTION OF *I, *Sr & *Cs.

| Days | Control | | | Experimental [$CaK_2Fe(CN)_6$], +$Ca(IO_3)_2$ + $CaCO_3$ (Oral) | | | Experimental PB + $KIO_3$ + Ca-Alginate (Diet) | | | Experimental [$CaK_2Fe(CN)_6$], +$Ca(IO_3)_2$ + $CaCO_3$ (Diet) | | |
|---|---|---|---|---|---|---|---|---|---|---|---|---|
| | $^{131}I$ | $^{85}Sr$ | $^{137}Cs$ | $^{131}I$ | $^{85}Sr$ | $^{137}Cs$ | $^{131}I$ | $^{85}Sr$ | $^{137}Cs$ | $^{131}I$ | $^{85}Sr$ | $^{137}Cs$ |
| 1 | 42 ± 5 | 65 ± 4 | 68 ± 5 | 26 ± 4 | 44 ± 3 | 52 ± 4 | 28 ± 3 | 45 ± 5 | 60 ± 6 | 32 ± 6 | 50 ± 4 | 56 ± 5 |
| 2 | 18 ± 2 | 58 ± 1 | 48 ± 2 | 10 ± 1 | 35 ± 2 | 24 ± 2 | 12 ± 2 | 36 ± 2 | 38 ± 2 | 18 ± 2 | 38 ± 2 | 35 ± 4 |
| 3 | 17 ± 3 | 48 ± 5 | 39 ± 4 | 9 ± 5 | 29 ± 4 | 18 ± 5 | 10 ± 4 | 30 ± 3 | 30 ± 5 | 14 ± 4 | 32 ± 3 | 28 ± 3 |
| 4 | 16 ± 4 | 36 ± 6 | 32 ± 5 | 8 ± 2 | 20 ± 1 | 16 ± 2 | 8 ± 2 | 20 ± 4 | 28 ± 1 | 12 ± 3 | 28 ± 4 | 22 ± 2 |
| 5 | 15 ± 2 | 28 ± 2 | 30 ± 3 | 7 ± 2 | 19 ± 2 | 14 ± 1 | 7 ± 3 | 19 ± 2 | 25 ± 4 | 10 ± 2 | 22 ± 3 | 15 ± 3 |
| 6 | 15 ± 1 | 26 ± 4 | 28 ± 2 | 7 ± 2 | 17 ± 3 | 12 ± 3 | 7 ± 1 | 18 ± 1 | 21 ± 3 | 8 ± 4 | 21 ± 4 | 13 ± 2 |
| 7 | 14 ± 2 | 25 ± 1 | 26 ± 1 | 6 ± 3 | 15 ± 2 | 10 ± 4 | 8 ± 2 | 16 ± 3 | 18 ± 2 | 7 ± 1 | 21 ± 3 | 12 ± 3 |
| 9 | 14 ± 1 | 23 ± 2 | 25 ± 4 | 4 ± 4 | 13 ± 4 | 9 ± 2 | 6 ± 3 | 14 ± 2 | 14 ± 1 | 6 ± 2 | 21 ± 3 | 11 ± 2 |
| 10 | 13 ± 2 | 20 ± 3 | 21 ± 1 | 3 ± 2 | 11 ± 2 | 7 ± 1 | 3 ± 4 | 12 ± 1 | 12 ± 2 | 4 ± 3 | 19 ± 2 | 9 ± 2 |
| 11 | 12 ± 1 | 19 ± 2 | 18 ± 4 | 2 ± 4 | 10 ± 2 | 5 ± 2 | 2 ± 1 | 10 ± 4 | 10 ± 2 | 3 ± 2 | 16 ± 3 | 6 ± 3 |
| 13 | 11 ± 2 | 15 ± 2 | 16 ± 2 | 2 ± 1 | 7 ± 2 | 3 ± 2 | 2 ± 2 | 9 ± 2 | 8 ± 2 | 2 ± 1 | 15 ± 2 | 3 ± 2 |
| 14 | 9 ± 1 | 9 ± 2 | 14 ± 3 | 1 ± 1 | 5 ± 2 | 1 ± 1 | 1 ± 1 | 8 ± 2 | 6 ± 2 | 2 ± 1 | 11 ± 2 | 1 ± 1 |

Results are Mean ± SD (6-7 animals/group) as % administered dose

Table 2 given hereunder shows comparatively the effect of the present mixture vis-à-vis the mixture of PB, $KIO_3$ and Calcium Gluconate administered orally after administration of a cocktail mixture of *Cs+*Sr+*I. The experimental animals were administered orally the new mixture, 2 hours after the administration of a cocktail of the three radionuclides. The whole body retention of each radionuclide was measured after 24 hours to 14 days. This has been compared to the mixture of Prussian Blue (PB)+$KIO_3$+Calcium gluconate which was administered orally.

TABLE 2

COMPARISON OF PRESENT MIXTURE [[$CaK_2Fe(CN)_6$] + $Ca(IO_3)_2$ + Ca-Gluconate] WITH (PB + $KIO_3$ + Ca-Gluconate) MIXTURE ON THE WHOLE BODY RETENTION OF *I, *Sr & *Cs

| | Control | | | Experimental [$CaK_2Fe(CN)_6$], +$Ca(IO_3)_2$ + CaG (Oral) | | | Experimental PB + $KIO_3$ + CaG (Oral) | | |
|---|---|---|---|---|---|---|---|---|---|
| Days | $^{131}I$ | $^{85}Sr$ | $^{137}Cs$ | $^{131}I$ | $^{85}Sr$ | $^{137}Cs$ | $^{131}I$ | $^{85}Sr$ | $^{137}Cs$ |
| 1 | 42 ± 3 | 65 ± 4 | 68 ± 5 | 24 ± 3 | 42 ± 4 | 52 ± 5 | 28 ± 4 | 45 ± 4 | 60 ± 1 |
| 2 | 18 ± 2 | 58 ± 2 | 48 ± 2 | 12 ± 2 | 35 ± 2 | 24 ± 2 | 12 ± 2 | 36 ± 2 | 38 ± 4 |
| 3 | 17 ± 5 | 48 ± 5 | 39 ± 4 | 9 ± 3 | 29 ± 3 | 18 ± 3 | 10 ± 3 | 30 ± 5 | 30 ± 3 |
| 4 | 16 ± 3 | 36 ± 6 | 32 ± 1 | 8 ± 2 | 20 ± 2 | 16 ± 2 | 8 ± 1 | 20 ± 3 | 28 ± 2 |
| 5 | 15 ± 2 | 28 ± 3 | 30 ± 2 | 7 ± 3 | 19 ± 3 | 14 ± 4 | 7 ± 2 | 19 ± 2 | 25 ± 1 |
| 6 | 15 ± 3 | 26 ± 2 | 28 ± 3 | 7 ± 2 | 17 ± 2 | 12 ± 1 | 7 ± 4 | 18 ± 3 | 21 ± 3 |
| 7 | 14 ± 2 | 25 ± 1 | 26 ± 2 | 6 ± 3 | 15 ± 3 | 10 ± 2 | 8 ± 2 | 16 ± 2 | 18 ± 2 |
| 9 | 14 ± 3 | 23 ± 2 | 25 ± 2 | 4 ± 1 | 13 ± 2 | 9 ± 2 | 6 ± 2 | 14 ± 1 | 14 ± 2 |

Results are Mean ± SD (6-7 animals/group) as % administered dose

Reference is now drawn to Table 3, which shows, the whole body retention count of *Cs using [$CaK_2Fe(CN)_6$] vis-à-vis Prussian Blue. As can be seen from the tables, CKF is twice as effective as PB in enhancing the clearance of *Cs from in vivo system of the affected subjects from 4-5 days onwards.

TABLE 3

WHOLE BODY RETENTION - $^{137}Cs$ (percent administered dose)

| Time (Days) | Cont. | Experimental PB | CKF |
|---|---|---|---|
| 0 | 100 | 100 | 100 |
| 1 | 77 ± 2 | 61 ± 10 | 55 ± 9 |
| 4 | 58 ± 5 | 31 ± 4 | 16 ± 7 |
| 8 | 44 ± 3 | 21 ± 3 | 10 ± 4 |
| 12 | 37 ± 6 | 15 ± 2 | 7 ± 3 |
| 16 | 32 ± 3 | 11 ± 2 | 5 ± 2 |
| 20 | 23 ± 3 | 7 ± 1 | 3 ± 1 |
| 24 | 19 ± 2 | 6 ± 1 | 3 ± 1 |
| 28 | 18 ± 2 | 5 ± 1 | 2 ± 1 |

Table 4 shows the percentage $^{131}I$, 24 hours post i.p. administration, where stable iodine in the form of $KIO_3$ and $Ca(IO_3)_2$ was given.

TABLE 4

Percent $^{131}I$-24 h post ip. administration.

| TISSUES | CONTROL | *$KIO_3$ (2 h post $^{131}I$) | $Ca(IO_3)_2$ (2 h post $^{131}I$) |
|---|---|---|---|
| BLOOD | 1.6 ± 0.4 | 1.6 ± 0.4 | 1.5 ± 0.1 |
| THYROID | 33 ± 1 | 10 ± 1 | 8 ± 1 |
| LIVER + GUT | 11 ± 0.5 | 16 ± 1 | 14 ± 1 |
| CARCAS | 21 ± 1 | 17 ± 2 | 14 ± 4 |

TABLE 4-continued

Percent $^{131}I$-24 h post ip. administration.

| TISSUES | CONTROL | *$KIO_3$ (2 h post $^{131}I$) | $Ca(IO_3)_2$ (2 h post $^{131}I$) |
|---|---|---|---|
| EXCRETA | 34 ± 1 | 64 ± 5 | 61 ± 3 |
| WBR | 62 ± 2 | 40 ± 2 | 39 ± 2 |

Table 5 shows percentage $^{131}I$, 24 hours post oral administration, where stable iodine in the form of $KIO_3$ and $Ca(IO_3)_2$ was administered orally. The results are means ±SD from 5-6 rats/group, as percent administered dose.

TABLE 5

Percent $^{131}I$-24 h post oral administration.

| TISSUES | CONTROL | $KIO_3$ (2 h post $^{131}I$) | $Ca(IO_3)_2$ (2 h post $^{131}I$) |
|---|---|---|---|
| BLOOD | 0.7 ± 0.05 | 0.6 ± 0.05 | 0.5 ± 0.05 |
| THYROID | 15 ± 1 | 4 ± 0.5 | 2 ± 0.5 |
| LIVER + GUT | 6 ± 0.4 | 7 ± 0.5 | 6 ± 1 |
| CARCAS | 11 ± 0.6 | 8 ± 0.5 | 8 ± 1 |
| EXCRETA | 66 ± 8 | 81 ± 1 | 83 ± 1 |
| WBR | 22 ± 1 | 14 ± 3 | 14 ± 2 |

Stable iodide (equivalent to 100 mg/70 Kg adult) in the form of $KIO_3$ and $Ca(IO_3)_2$ is given orally.

Table 6 shows the comparison of $Ca(IO_3)_2$ with $KIO_3$ on the whole body retention of radioiodine. Stable iodine (equivalent to 100 mg/70 Kg adult per day) in the form of $KIO_3$ and $Ca(IO_3)_2$ is mixed with their diet.

TABLE 6

COMPARISON OF $Ca(IO_3)_2$ WITH $KIO_3$ ON THE WHOLE BODY RETENTION OF RADIO-IODINE.

| DAYS | CONTROL | $KIO_3$ (2 h post i.p. $^{131}I$) | $Ca(IO_3)_2$ (2 h post i.p. $^{131}I$) |
|---|---|---|---|
| 1 | 42 ± 5 | 28 ± 3 | 32 ± 6 |
| 2 | 18 ± 2 | 12 ± 2 | 15 ± 2 |
| 3 | 17 ± 3 | 10 ± 4 | 14 ± 4 |
| 4 | 16 ± 4 | 8 ± 2 | 12 ± 3 |
| 5 | 15 ± 2 | 7 ± 3 | 10 ± 2 |

TABLE 6-continued

COMPARISON OF $Ca(IO_3)_2$ WITH $KIO_3$ ON THE WHOLE BODY RETENTION OF RADIO-IODINE.

| DAYS | CONTROL | $KIO_3$ (2 h post i.p. $^{131}$I) | $Ca(IO_3)_2$ (2 h post i.p. $^{131}$I) |
|---|---|---|---|
| 6 | 15 ± 1 | 7 ± 1 | 8 ± 4 |
| 7 | 14 ± 2 | 8 ± 2 | 7 ± 1 |
| 9 | 14 ± 1 | 6 ± 3 | 6 ± 2 |
| 10 | 13 ± 2 | 3 ± 4 | 4 ± 3 |
| 11 | 12 ± 1 | 2 ± 1 | 3 ± 2 |
| 13 | 11 ± 2 | 2 ± 2 | 2 ± 1 |
| 14 | 9 ± 1 | 1 ± 1 | 2 ± 1 |

Table 7 shows the comparison of $Ca(IO_3)_2$ with $KIO_3$ on the whole body retention of radioiodine when the stable iodine (equivalent to 100 mg/70 Kg adult per day) in the form of $KIO_3$ and $Ca(IO_3)_2$ is administered orally.

TABLE 7

COMPARISON OF $Ca(IO_3)_2$ WITH $KIO_3$ ON THE WHOLE BODY RETENTION OF RADIO-IODINE.

| DAYS | CONTROL | $KIO_3$ (2 h post i.p. $^{131}$I) | $Ca(IO_3)_2$ (2 h post i.p. $^{131}$I) |
|---|---|---|---|
| 1 | 42 ± 3 | 28 ± 4 | 24 ± 3 |
| 2 | 18 ± 2 | 12 ± 2 | 12 ± 2 |
| 3 | 17 ± 5 | 10 ± 3 | 9 ± 3 |
| 4 | 16 ± 3 | 8 ± 1 | 8 ± 2 |
| 5 | 15 ± 2 | 7 ± 2 | 7 ± 3 |
| 6 | 15 ± 3 | 7 ± 4 | 7 ± 2 |
| 7 | 14 ± 2 | 8 ± 2 | 6 ± 3 |
| 9 | 14 ± 3 | 6 ± 2 | 4 ± 1 |

Table 8 shows the percentage binding capacity of *Cs at different pH ranges (2-7). This data shows that Prussian blue, at the same dose level is only 25-50% as effective as $[CaK_2Fe(CN)_6]$ in complexing/extraction of stable/radio Cesium in acidic medium.

TABLE 8

PERCENT BINDING CAPACITY AT DIFFERENT pH - RANGES.

| pH | Control | Prussian Blue (PB) | Calcium Potassium Ferrocyanide (CKF) $[CaK_2Fe(CN)_6]$, |
|---|---|---|---|
| 2 | 2.0 ± 0.4 | 27 ± 2 | 99 ± 0.9 |
| 3 | 2.0 ± 0.4 | 58 ± 0.7 | 100 ± 0.9 |
| 4 | 2.0 ± 0.6 | 75 ± 0.4 | 98 v 0.9 |
| 5 | 2.0 ± 0.4 | 75 ± 0.3 | 97 ± 0.9 |
| 6 | 2.0 ± 0.5 | 67 ± 0.6 | 97 ± 0.9 |
| 7 | 2.0 ± 0.6 | 59 ± 0.9 | 98 ± 0.9 |

Results are Mean ± S.D. from 4-5 samples at each point/group.

The term 'emergency' referred to within this specification shall be construed to include:

(a) The event of an accidental release of the radioisotopes in the environment due to any nuclear accident.

(b) Any accidental release of the hazardous nuclides in the environment.

(c) A nuclear fallout including that occurring in the normal course of an experimental, diagnostic or therapeutic purpose.

(d) Any kind of accidental uptake and retention of the radionuclides by the human or animal subjects.

(e) Any other kind of exposure to the volatile radionuclides.

(f) Any kind of a radiological accident.

The acronym CKF appearing in the text and the accompanying tables and figures refers to the compound Calcium Potassium Ferrocyanide.

The foregoing examples and formulations are presented for the purpose of illustration and are not intended to limit the scope of the invention. Variations and changes, which are obvious to one skilled in the art, are intended to be within the scope and nature of the invention as defined in the appended claims.

The invention claimed is:

1. A method comprising:
administering Calcium Potassium Ferrocyanide $CaK_2[Fe(CN)_6]$, wherein administering is effective for decorporating radiocesium from an in-vivo system.

2. A prophylactic composition for oral administration for the simultaneous decorporation of radiocesium, radiostrontium and radioiodine from in vivo milieu of subjects affected by the exposure to nuclear radiation, said composition comprising calcium carbonate, calcium iodate and calcium potassium ferrocyanide.

3. A prophylactic composition as claimed in claim 2, comprising 1000-1500 mg calcium carbonate, 45-65 mg calcium iodate and 900-1100 mg calcium potassium ferrocyanide.

4. A prophylactic composition as claimed in claim 3 comprising 1100-1400 mg calcium carbonate, 50-60 mg calcium iodate and 950-1050 mg calcium potassium ferrocyanide.

5. A prophylactic composition as claimed in claim 4, comprising 1200-1300 mg calcium carbonate, 52-56 mg calcium iodate and 980-1020 mg calcium potassium ferrocyanide.

6. A prophylactic composition as claimed in claim 2, wherein said composition is in the form of suspension, tablets or capsules.

7. A prophylactic composition as claimed in claim 6, wherein said composition is formulated in the form of a suspension in 12-15 ml of water, soda, soft drink or fruit juice.

8. A prophylactic composition as claimed in claim 6, wherein said composition is in the form of tablets.

9. A prophylactic composition as claimed in claim 6, wherein said composition is in the form of capsules.

10. A prophylactic composition as claimed in claim 2, wherein 2-4 tablets or capsules or chewable tablets are administered to a human subject once a day.

11. A prophylactic composition as claimed in claim 2, wherein said composition is formulated in smaller doses comprising 50% by weight of each of the said constituents to be suitable to children.

12. A prophylactic composition as claimed in claim 11, comprising 500-750 mg of calcium carbonate, 20-35 mg of calcium iodate and 450-550 mg of calcium potassium ferrocyanide.

13. A prophylactic composition as claimed in claim 12, comprising 550-700 mg of calcium carbonate, 25-30 mg of calcium iodate and 475-525 mg of calcium potassium ferrocyanide.

14. A prophylactic composition as claimed in claim 11, wherein 2 to 4 tablets or capsules or chewable tablets of said composition provide the dosage to be administered to a child once a day.

15. A method comprising:
administering a composition comprising calcium potassium ferrocyanide ($[CaK_2Fe(CN)_6]$), calcium iodate and calcium carbonate for the simultaneous decorporation of radiocesium, radiostrontium and radioiodine from in vivo milieu of subjects affected by the exposure to nuclear radiation.

* * * * *